United States Patent
Stoll et al.

(10) Patent No.: US 9,339,321 B2
(45) Date of Patent: May 17, 2016

(54) ANGLED INSTRUMENT ASSEMBLY

(71) Applicant: Lanx, Inc., Broomfield, CO (US)

(72) Inventors: Caleb Stoll, Westminster, CO (US);
Allison Capote, Boulder, CO (US);
Corneliu Vlad, Littleton, CO (US)

(73) Assignee: ZIMMER BIOMET SPINE, INC., Broomfield, CO (US)

( * ) Notice: Subject to any disclaimer, the term of this patent is extended or adjusted under 35 U.S.C. 154(b) by 255 days.

(21) Appl. No.: 13/913,158

(22) Filed: Jun. 7, 2013

(65) Prior Publication Data

US 2014/0364855 A1    Dec. 11, 2014

(51) Int. Cl.
*A61B 17/00*    (2006.01)
*A61B 17/88*    (2006.01)
*A61B 17/16*    (2006.01)

(52) U.S. Cl.
CPC .......... *A61B 17/8875* (2013.01); *A61B 17/1631* (2013.01); *A61B 17/1624* (2013.01); *A61B 17/1633* (2013.01)

(58) Field of Classification Search
CPC ........... A61B 17/8875; A61B 17/8886; A61B 17/1631; A61B 17/1633; A61B 17/1624
USPC ................................. 81/177.7, 177.8, 177.75
See application file for complete search history.

(56) References Cited

U.S. PATENT DOCUMENTS

| | | | |
|---|---|---|---|
| 6,187,007 B1 | 2/2001 | Frigg et al. | |
| 8,740,983 B1 * | 6/2014 | Arnold | A61F 2/4455 623/17.16 |
| 2004/0172036 A1 | 9/2004 | Dye | |
| 2008/0188854 A1 | 8/2008 | Moser | |
| 2012/0143195 A1 | 6/2012 | Sander | |

FOREIGN PATENT DOCUMENTS

JP         2013046787 A    3/2013
WO    WO-2014197776 A1    12/2014

OTHER PUBLICATIONS

International Search Report and Written Opinion from counterpart application PCT/US2014/041252 (Sep. 25, 2014).

* cited by examiner

*Primary Examiner* — Christopher Beccia
*Assistant Examiner* — Diana S Jones
(74) *Attorney, Agent, or Firm* — Schwegman Lundberg & Woessner, P.A.

(57) ABSTRACT

An angled instrument assembly includes an angled sleeve, a driver shaft, and a tool bit. The angled sleeve includes a straight passage segment that meets an angled passage segment at a junction. The junction includes an inner elbow and an outer elbow. Material is removed from the inner surface of the inner elbow in order to improve the ease with which the driver shaft can be moved in and out of the angled sleeve. The assembly can also include drafted female or male engagement bodies for facilitating the engagement and disengagement of the tool bit with a tool bit engagement assembly located at the distal end of the driver shaft.

16 Claims, 20 Drawing Sheets

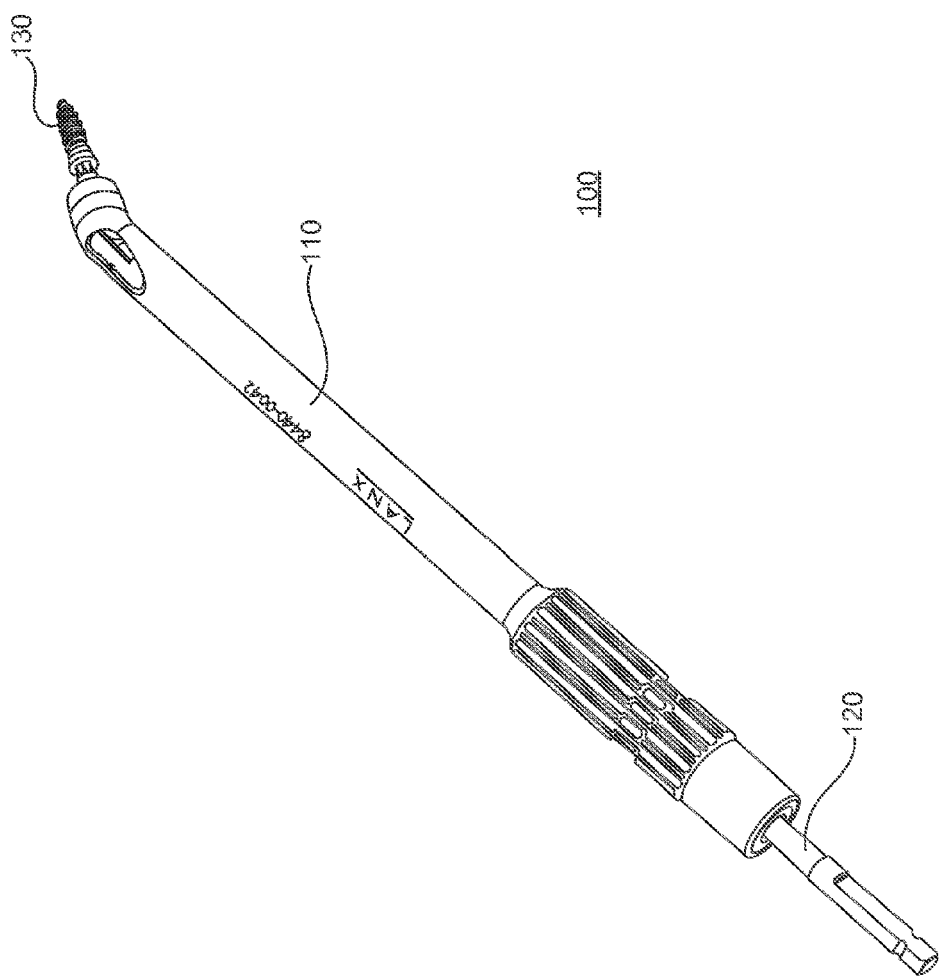

ANGLED INSTRUMENT ASSEMBLY

BACKGROUND

Many surgical procedures require access to a target site within the human body where it is not possible to provide a straight passage. For example, obstructions created by the human anatomy and/or other surgical instruments being used for retraction of soft tissues or other purposes can prevent the availability of a straight passage. In such instances, it becomes difficult or impossible to use a straight instrument to access the target site.

Numerous devices have been developed in an attempt to address this problem. In one example, a drilling or screwing tool having a U-joint at the terminal end is used in conjunction with an instrument that guides the tip of the tool to the target site. This system is complicated because of the need for multiple instruments to carry out the drilling or screwing. In another example, crown gears are used at the end of the tool, but these crown gears tend to wear easily. Moreover, to keep the gear from slipping, a significant amount of force needs to be applied, which increases the wear and may fatigue the user of the device. In still another example, sleeves are used to guide a drilling or screwing tool to the target site, but these sleeves are typically large and bulbous.

SUMMARY

Described herein are various embodiments of an angled instrument assembly that overcome some or all of the problems associated with previously known devices to access a target site when straight line access to the target site is not available.

In some embodiments, the angled instrument assembly includes an angled sleeve, a driver shaft having a tool bit engagement assembly provided at the distal end thereof, and a tool bit used to, for example, drive a screw or drill a hole into the target site.

The angled sleeve generally includes a straight passage segment and an angled passage segment located at the distal end of the sleeve. The straight passage segment and angled passage segment meet at a junction and define a generally hollow passage. At the inner elbow of the junction, a portion of the interior surface is removed to create an intermediate interior surface segment having an axis that is not parallel to either the axis of the straight passage segment or the axis of the angled passage segment. In some embodiments, the angle formed by the axis of the intermediate interior surface segment created at the junction and the axis of the straight passage segment is greater than zero but less than the angle formed by the axis of the straight passage segment and the axis of the angled passage segment.

The driver shaft is configured to be received with in the hollow passage of the angled sleeve. The driver shaft includes a tool bit engagement assembly at the distal end of the driver shaft. The tool bit engagement assembly provides a fork at the distal end of the assembly that is capable of pivoting about two separate axes that are perpendicular to one another. The distal end of the fork also includes a recess configured to engage an engagement body of a tool bit.

The tool bit includes the aforementioned engagement body at the proximal end and a tool body at the distal end. The side walls of the engagement body are slightly drafted, such as at an angle of from 0.1° to 5°.

In application, the tool bit is positioned at the distal end of the angled sleeve and the driver shaft is then inserted into the angled sleeve and moved axially towards the distal end of the angled sleeve until the recess in the fork engages with the engagement body of the tool bit. In this configuration, rotation of the driver shaft at a location along the straight passage segment of the angled sleeves rotates the fork and the engaged tool bit and provides a screwing or drilling motion.

Removal of the interior surface of the angled sleeve at the inner elbow of the junction of the angled sleeve and slightly drafting the side walls of the engagement body of the tool bit can both improve the ability to move the driver shaft out of the angled sleeve. The drafted side walls allow the fork to more easily disengage from the engagement body of the tool bit. The removed interior surface at the inner elbow of the junction of the angled sleeve allows the tool bit engagement assembly to move more easily through the junction of the angled sleeve.

Other benefits can also be achieved by the angled instrument assembly described herein. The disclosed instrument is simpler and more intuitive than other prior art devices. The instrument is also modular, in that a variety of different tool bits can be used interchangeably with the same angled sleeve and driver shaft. The instrument can also be easier to sterilize relative to some prior art devices.

BRIEF DESCRIPTION OF THE DRAWINGS

Various examples of the present invention will be discussed with reference to the appended drawings. The drawings depict only illustrative examples of the invention and are not to be considered limiting in scope.

FIG. 1A is a perspective view of an angled tool assembly according to various embodiments described herein.

DETAILED DESCRIPTION

Figure 1B:
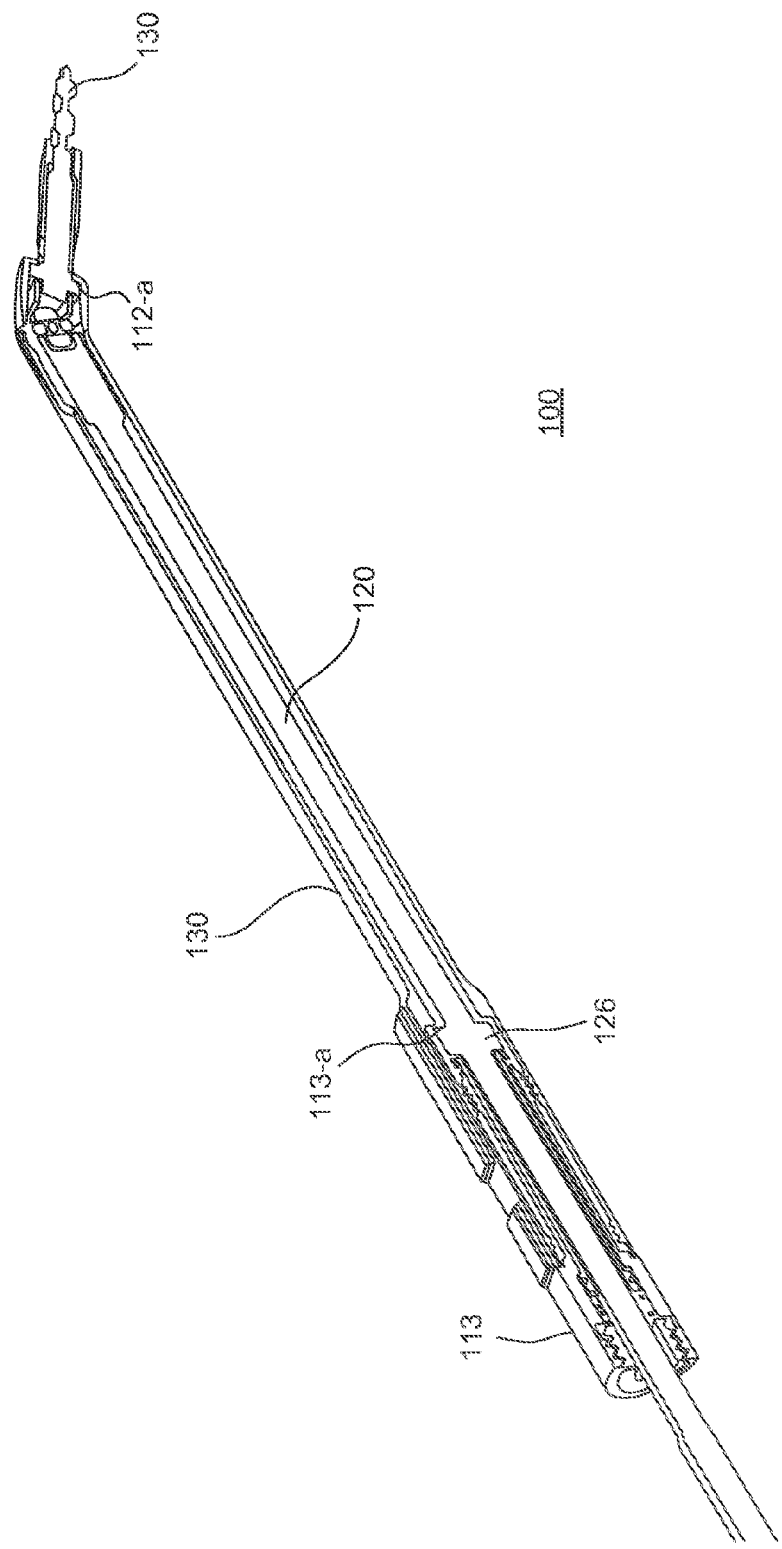
FIG. 1B is a cross sectional view of the angled tool assembly shown in FIG. 1A.

Embodiments of an angled instrument assembly described herein generally include an angled sleeve, a driver shaft, and an interchangeable tool bit. The angled instrument assembly may be configured to drive a screw in surgical procedures where a straight passageway is not available. The angled instrument assembly may include design features to allow the driver shaft to move axially through the angled shaft more freely and without resistance sometimes experienced in prior art devices designed for similar uses. These design features may include removing a portion of the interior surface of the angled sleeve at the junction between the straight passage segment and the angled passage segment so as to create an intermediate angled interior surface that is greater than 0° but less than the angle of the angled passage segment. In some embodiments, the intermediate angled interior surface is removed only from the inner elbow region of the junction of the angled sleeve. Another design feature that may improve the movement of the driver shaft through the angled sleeve is to provide the male engagement body of the tool bit with drafted side edges. In some embodiments, the side edges of the male engagement body of the tool bit are drafted in the range of from 0.1° to 5°.

With reference to FIGS. 1A, 1B, 2, 3A and 3B, perspective and cross sectional views of an angled instrument assembly 100 according to various embodiments are provided. The angled instrument assembly 100 includes an angled sleeve 110, a driver shaft 120, and a tool bit 130. The driver shaft 120 is configured to be received within the angled sleeve 110. The distal end of the driver shaft 120 is inserted into proximal end 110-a of the angled sleeve 110. The angled sleeve 110 includes a tool bit opening 114 at the distal end 110-b of the angled sleeve 110 sized to receive the tool bit 130 and allow the tool bit 130 to move into and through the angled passage segment 112 of the angled sleeve 110 until at least a portion of the tool bit 130 extends out of the distal end 110-b of the angled sleeve 110. When the tool bit 130 is so positioned, the distal end 121-b of the driver shaft 120 is inserted into the angled shaft 110 at the proximal end 110-a and moved towards the distal end 110-b of the angled shaft 110 until the distal end 121-b of the driver shaft 120 engages with the proximal end 132 of the tool bit 130 (via a mechanism described in greater detail below). A user can then rotate the tool bit 130 by rotating the driver shaft 120 (either directly or via a handle 113 on the proximal end 110-a of the angled sleeve 110 that engages the driver shaft 120).

Figure 2:
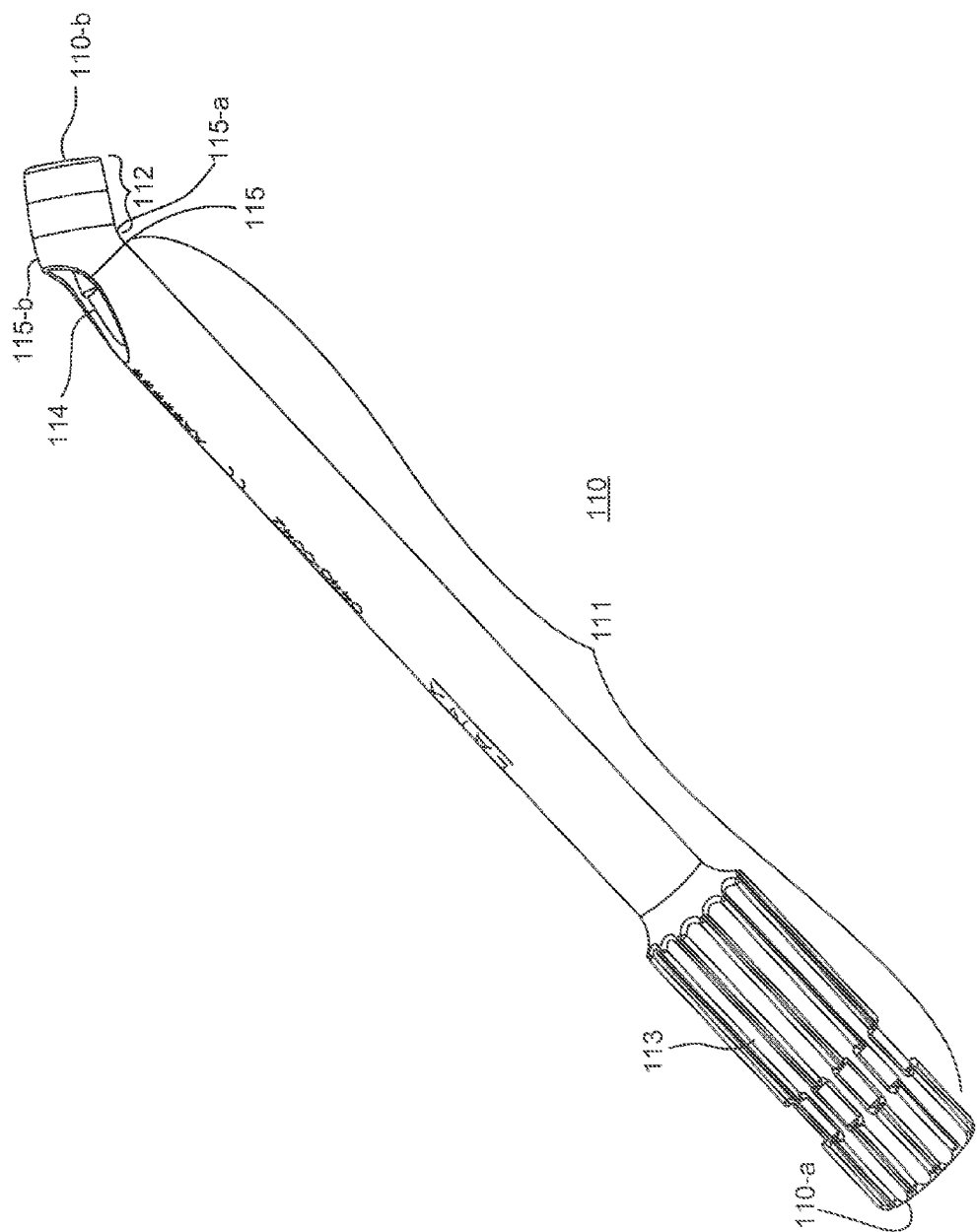
FIG. 2 is a perspective view of an angled sleeve according to various embodiments described herein.

With reference to FIG. 2, the angled sleeve 110 has a proximal end 110-a and a distal end 110-b. The proximal end 110-a and the distal end 110-b each provide an opening into a generally cylindrical hollow passage defined by the angled sleeve 110. The angled sleeve 110 includes a straight passage segment 111 and an angled passage segment 112. The diameter of the cylindrical hollow passage is generally uniform in both passages, with the possible exception being the proximal end of the straight passage segment 111. In some embodiments, the proximal end of the straight passage segment 111 can have a larger diameter in order to accommodate a cap and/or a mechanism used to rotate the drive shaft 120 positioned within the angled sleeve 110.

The straight passage segment 111 generally extends from the proximal end 110-a of the angled sleeve 110 to a location near the distal end 110-b of the angled sleeve 110. The straight passage segment 111 is longer than the angled passage segment 112, and in some embodiments is several times longer than the angled passage segment 112. The straight passage segment 111 is generally long enough such that a majority or all of the driver shaft 120 can be received inside of the straight passage segment 111. In some embodiments, the driver shaft 120 is longer than the straight passage segment 111 such that when the distal end 121-b of the driver shaft 120 is at the distal end of the straight passage segment, the proximal portion of the driver shaft 120 extends out of the proximal end 110-a of the angled sleeve 110.

Figure 3A:
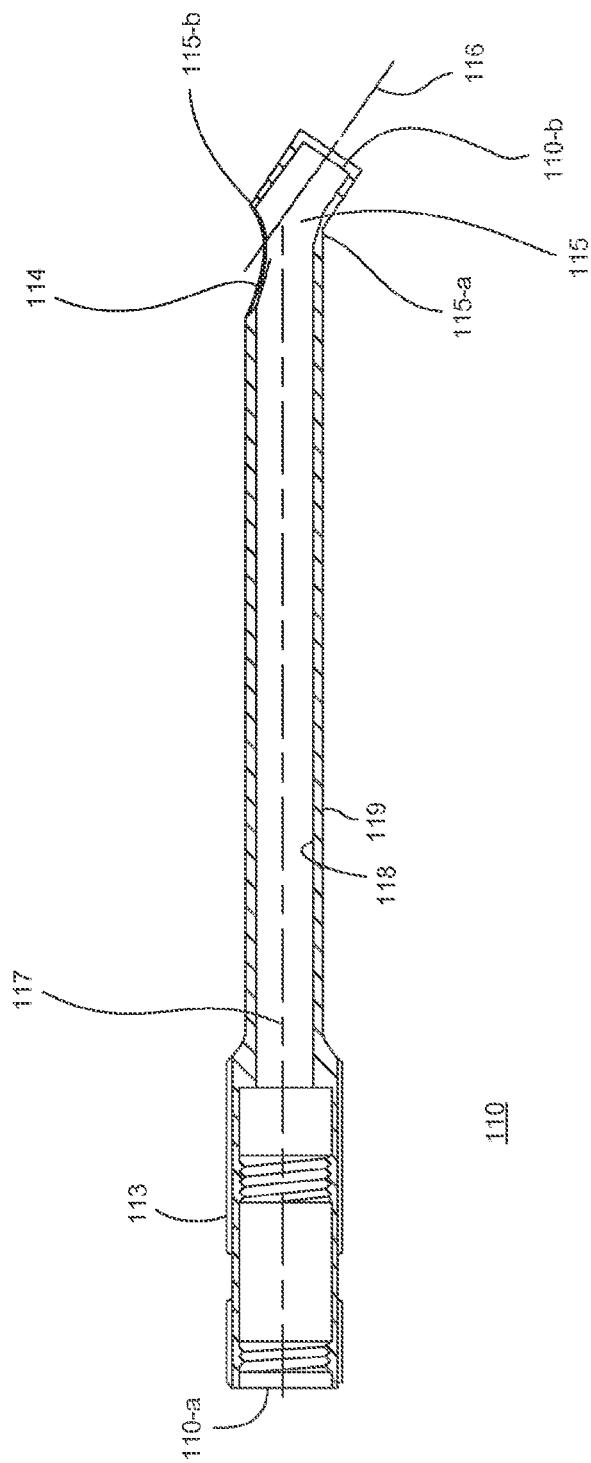
FIG. 3A is a cross sectional view of a distal end of an angled sleeve according to various embodiments described herein.
Figure 3B:
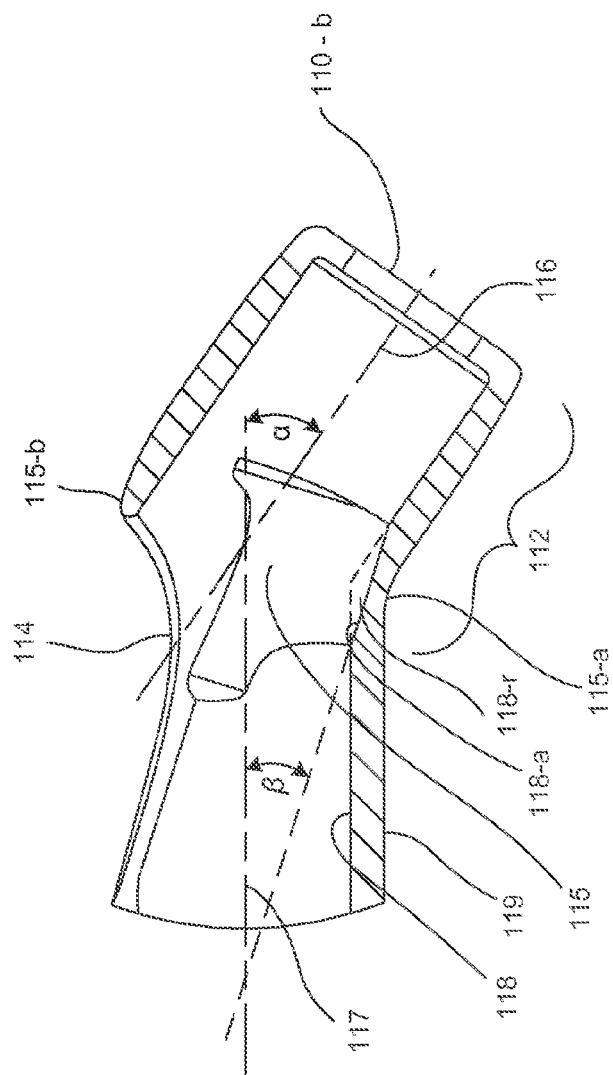
FIG. 3B is a cross sectional view of a an angled sleeve according to various embodiments described herein.

The angled passage segment 112 is located at the distal end 110-b of the angled sleeve 110. The angled passage segment 112 meets the straight passage segment 111 at a junction 115 and creates an inner elbow region 115-a and an outer elbow region 115-b. With reference to FIGS. 3A and 3B, the longitudinal axis 116 of the angled passage segment 112 intersects the longitudinal axis 117 of the straight passage segment 111 to define an angle ALPHA. Angle ALPHA may be in the range of from about 1° to 45°. In some embodiments, angle ALPHA is in the range of from 30° to 40°. In some embodiments, angle ALPHA is about 35°.

With continuing reference to FIGS. 3A and 3B, the angled sleeve 110 includes an interior surface 118 and an exterior surface 119. The distance between the interior surface 118 and the exterior surface 119 is the thickness of the walls of the angled sleeve 110. In some embodiments, the thickness is generally uniform throughout the angled sleeve 110. In one aspect, however, the inner elbow region 115-a may have a reduced thickness to improve the ability of the driver shaft 120 to move in and out of the angled sleeve 110. With specific reference to FIG. 3B, a portion of the wall of the angled sleeve 110 is removed from the inner surface 118 at the inner elbow region 115-a so that the thickness of the wall at the inner elbow region 115-a is reduced. The removed portion 118-r is shown in phantom for reference. The portion of the inner surface 118 removed from this region is removed in a manner that leaves behind a surface 118-a having an axis that is not parallel with the axis of the interior surface 118 of the angled passage segment 112 or the axis of the straight passage segment 111. The axis of the surface 118-a forms an angle BETA with the axis 117 of the straight passage segment 111. The angle BETA is greater than zero and less than the angle ALPHA. In some embodiments, the angle BETA is from about 1° to less than 45°. In some embodiments, the angle BETA is in the range of from about 15° to 20°. In some embodiments, the angle BETA is from 0.25 to 0.75 times the angle ALPHA. In some embodiments, the angle BETA is 0.5 times the angle ALPHA.

Figure 13:
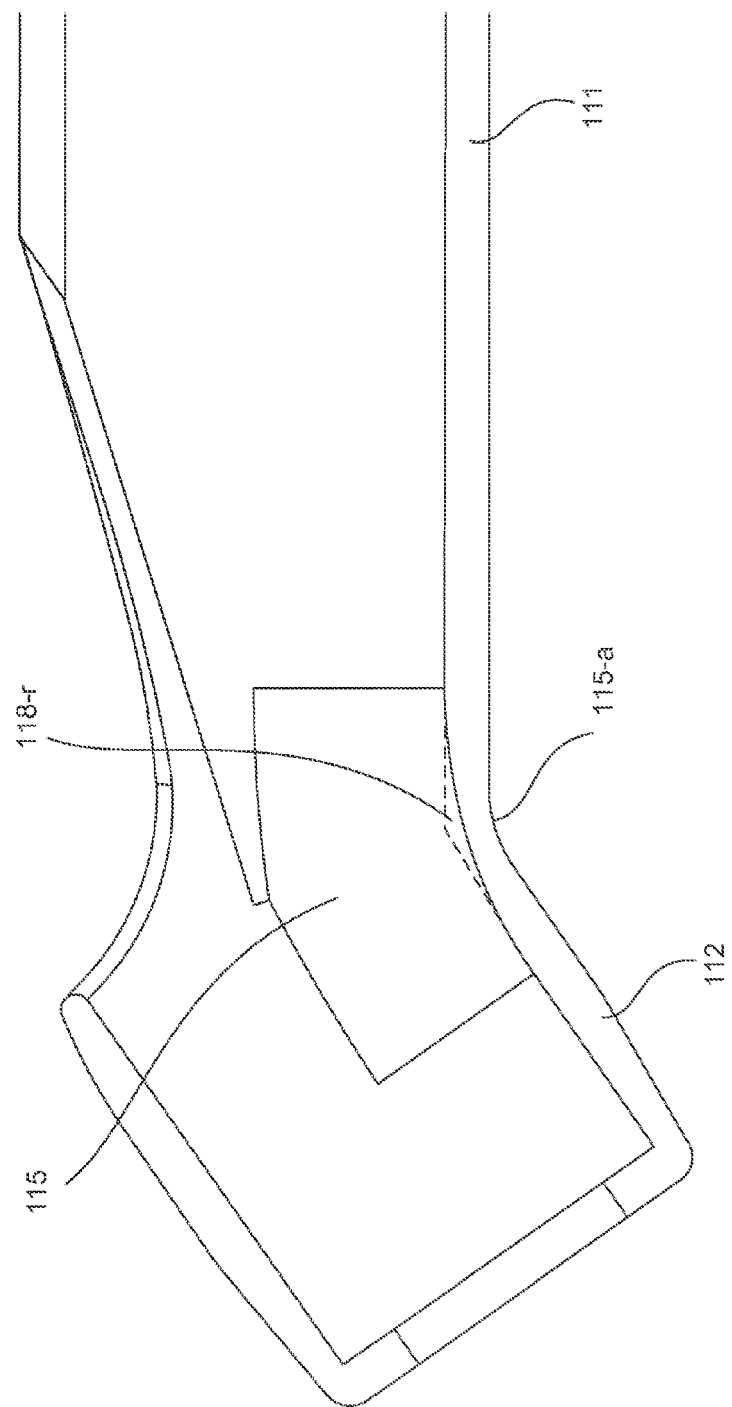
FIG. 13 is a cross sectional view of an angled sleeve according to various embodiments described herein.

In some alternate embodiments, the interior surface of the inner elbow region 115-a is curved to provide a gradual transition between the straight passage segment 111 and the angled passage segment 112. As shown in FIG. 13, the curved interior surface of the inner elbow region 115-a provides a similar removal of material at the inner elbow region 115-a of the angled sleeve 110. Removed portion 118-r shown in phantom for reference illustrates the amount of material removed from the inner elbow region 115-a when the inner surface of this inner elbow region 115-a is curved. As in the previously described embodiment, the removed material at the inner elbow region 115-a of the junction 115 improves the mobility of the driver shaft 120 in and out of the angled sleeve 110.

Figure 14:
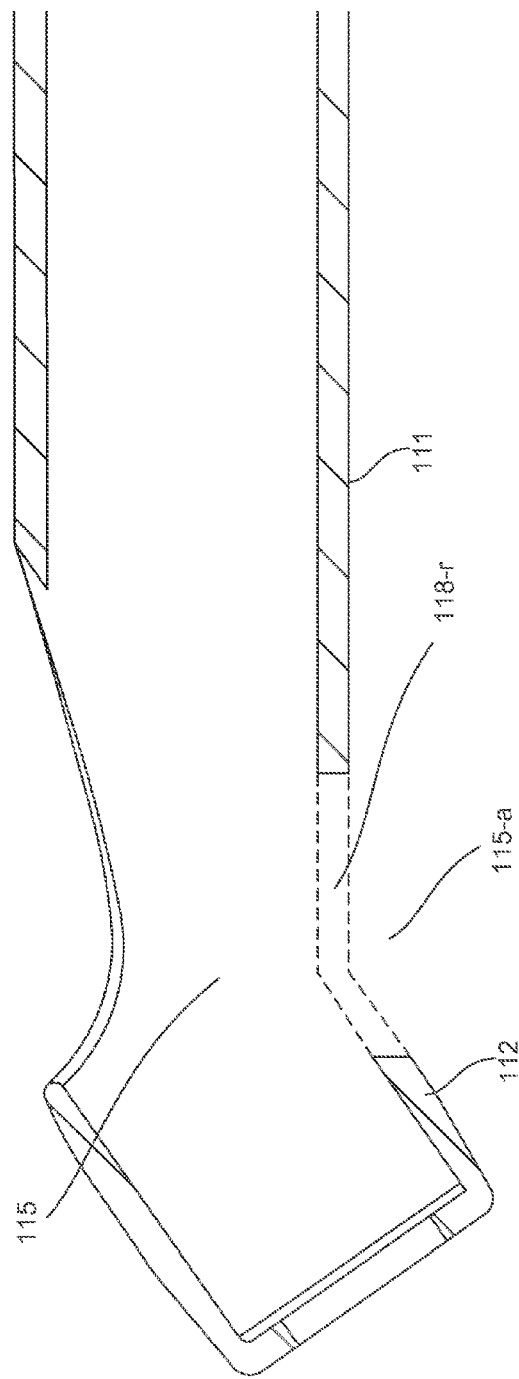
FIG. 14 is a cross sectional view of an angled sleeve according to various embodiments described herein.

In still other alternate embodiments, an opening is provided at the inner elbow region 115-a of the junction 115. As shown in FIG. 14, the opening is located at the inner elbow region 115-a and is intermediate the distal end of the straight passage segment 111 and the angled passage segment 112. Removed portion 118-r is shown in phantom for reference illustrate the amount of material removed from the inner elbow region 115-a to create the opening. As in the previously described embodiments, the removed material at the inner elbow region 115-a of the junction 115 improves the mobility of the driver shaft 120 in and out of the angled sleeve 110.

Any other manner in which the vertex formed by the inner surface of the straight passage segment 111 meeting the inner surface of the angled passage segment 112 is removed can be used in order to provide the additional space at the inner elbow region 115-a needed to improve the mobility of the driver shaft 120 through the angled sleeve 110.

As noted above, the angled sleeve 110 also includes a tool bit opening 114 near the distal end 110-b of the angled sleeve 110. The tool bit opening 114 is provided generally at the outer elbow region 115-b and can extend across both a portion of the straight passage segment 111 and the angled passage segment 112. The shape of the tool bit opening 114 is shaped to allow tool bits to be inserted and removed from the angled sleeve 110 and is shown as generally oval or tear drop shaped, although other shapes are usable. The tool bit opening 114 is sized and positioned such that the longitudinal axis of a tool bit can be oriented parallel to the axis 116 of the angled passage segment 112 and passed directly into the angled passage segment 112 via the tool bit opening 114. The tool bit opening 114 is positioned on the generally straight passage segment 111 at the outer elbow region 115-b such that the distal end 121-b of the drive shaft 120 freely moves past the tool bit opening 114.

In some embodiments, an opening 114 is not required for positioning a tool bit at the distal 110-b end of the angled sleeve. In some embodiments, the dimensions of the tool bit are sufficiently small that the tool bit can be inserted into the angled sleeve 110 at the proximal end 110-a and moved through the angled sleeve 110, including through the junction 115, until is reaches the distal end 110-b of the angled sleeve.

Figure 4A:
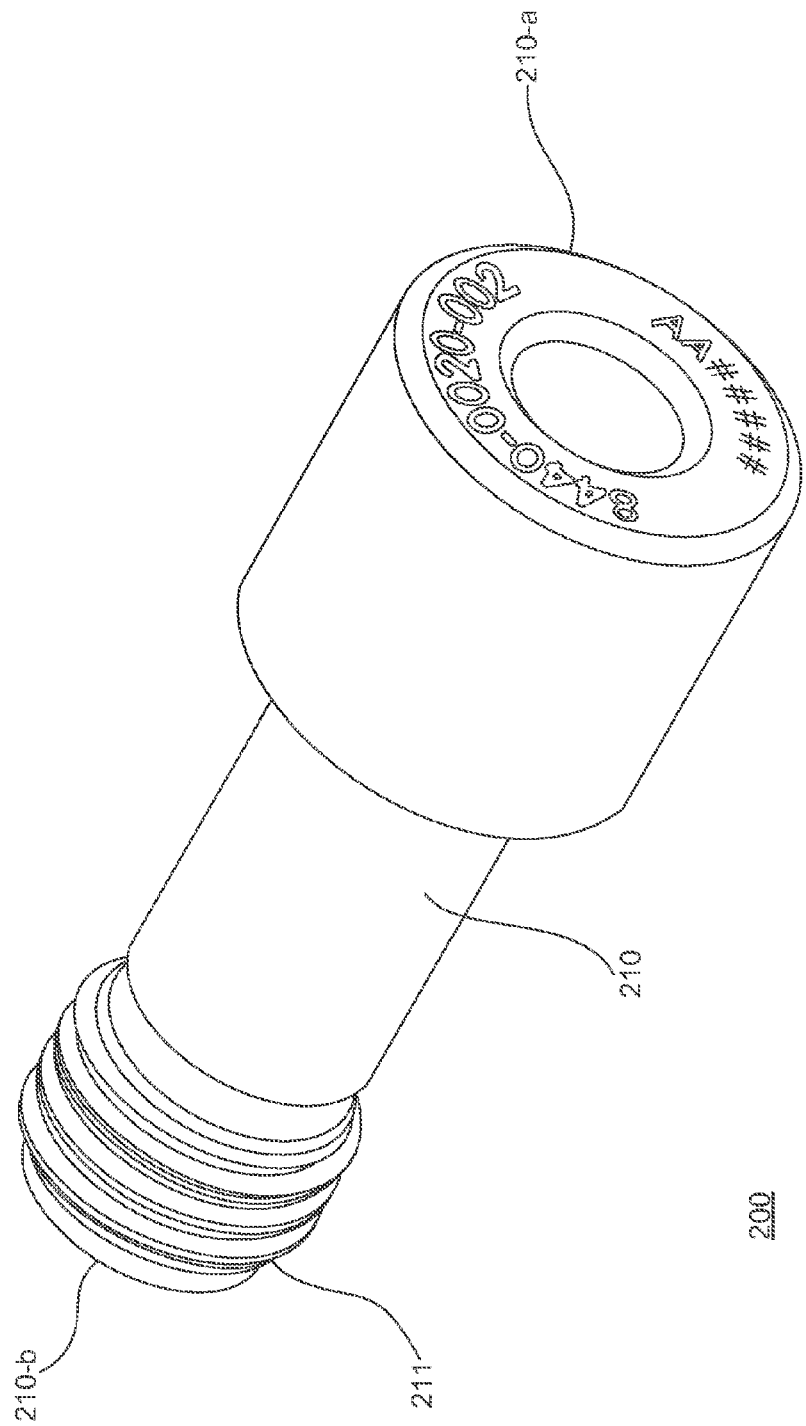
FIG. 4A is a perspective view of a sleeve cap suitable for use with the angled sleeve according to various embodiments described herein.
Figure 4B:
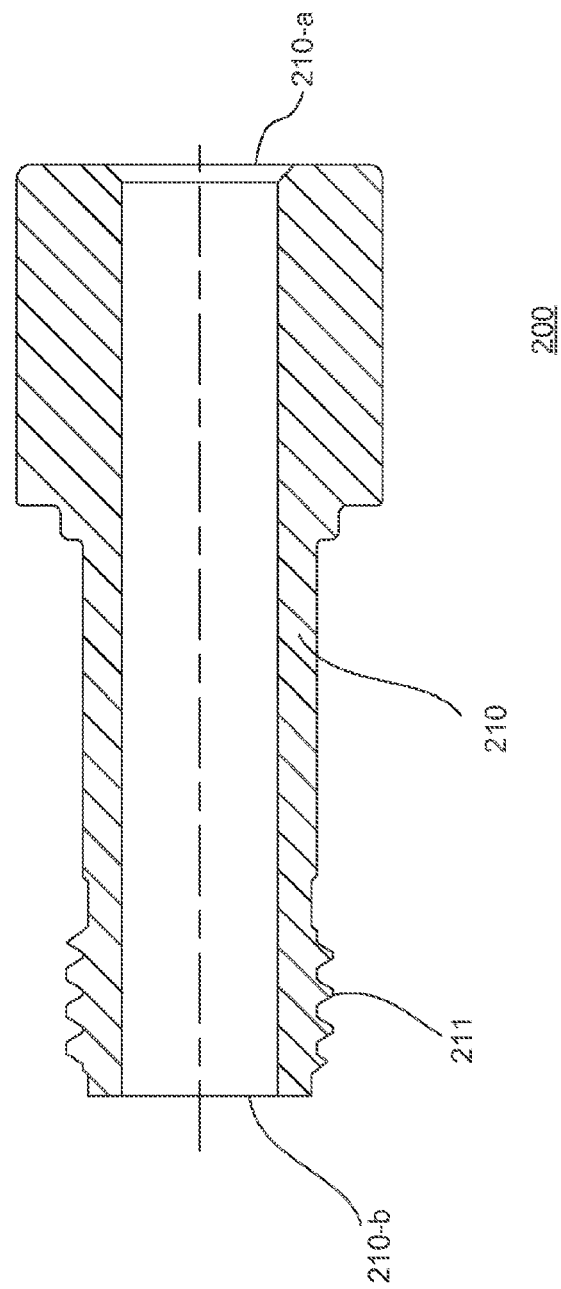
FIG. 4B is a cross sectional view of the sleeve cap shown in FIG. 4A.
Figure 4C:
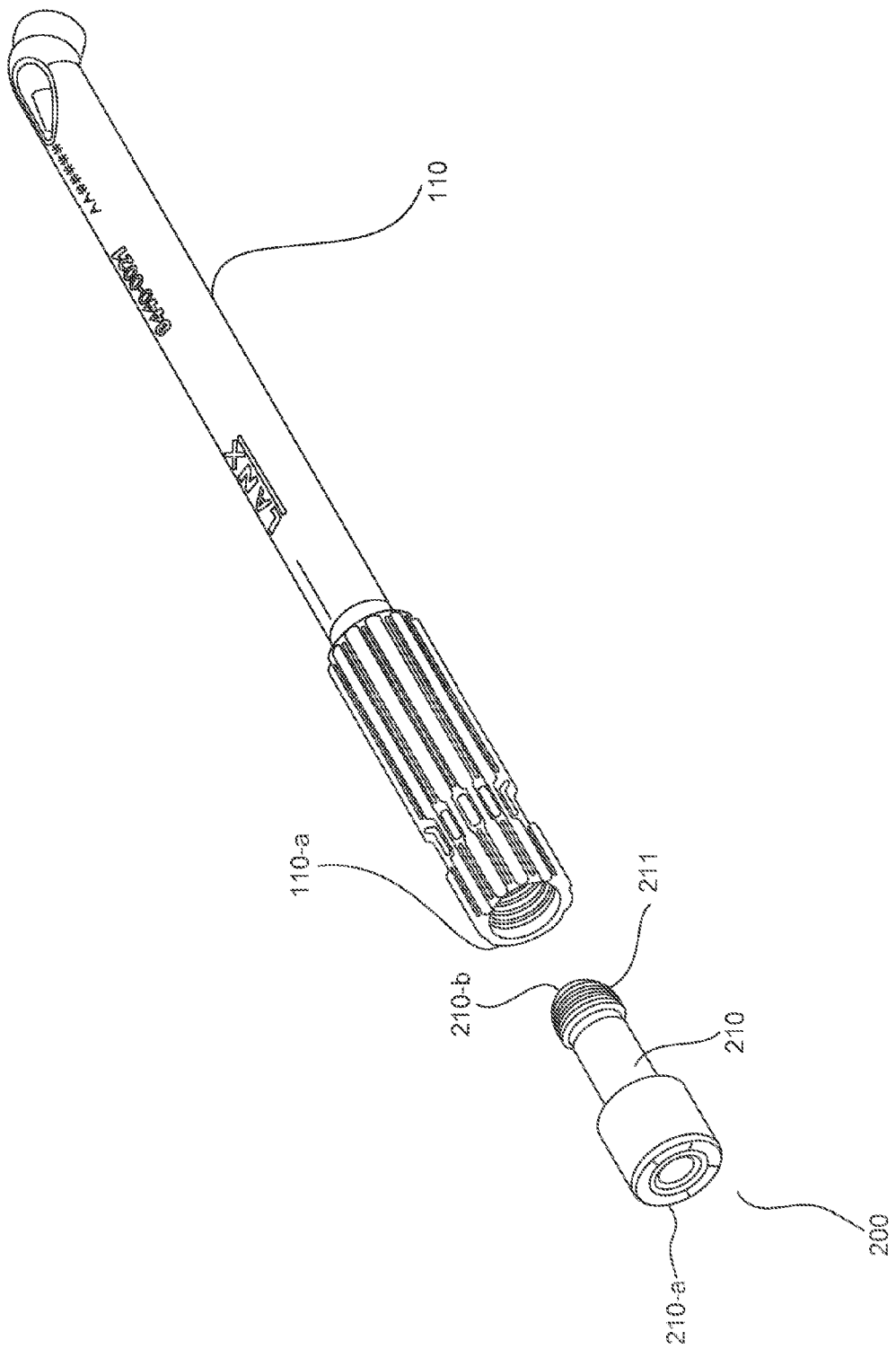
FIG. 4C is a perspective view of an angled sleeve and a sleeve cap according to various embodiments described herein.

In some embodiments, the angled sleeve 110 further includes a sleeve cap 200. With reference to FIGS. 4A, 4B, and 4C the sleeve cap 200 generally includes a cylindrical body 210 having a proximal end 210-a and a distal end 210-b and a cylindrical hollow passage extending from the proximal end 210-a to the distal end 210-b. The hollow passage can be dimensioned such that the driver shaft 120 can pass through the hollow passage. The outer diameter of the cylindrical body is smaller at the distal end 210-b than at the proximal end 210-a. The diameter of the cylindrical body at the distal end 210-b is generally equal to or less than the diameter of the hollow passage at the proximal end 110-a of the angled sleeve 110 so that the distal end 210-a can be inserted into the hollow passage at the proximal end 110-a of the angled sleeve 110. The distal end 210-b can also include threading 211 that is designed to mate with threading located in the hollow passage at the proximal end 110-a of the angled sleeve 110. In this manner, the sleeve cap 200 may be secured to the angled sleeve 110. At the proximal end 210-b, the cylindrical body 210 may have a diameter that is approximately equal to the outer diameter of the angled sleeve 110 at the proximal end 110-a. In this manner, the proximal end 210-a of the cylindrical body 210 can be coextensive and flush mounted with the proximal end 110-a of the angled sleeve 110 when the distal end 210-b of the cylindrical body 210 is inserted into the proximal end 110-a of the angled sleeve.

Figure 5A:
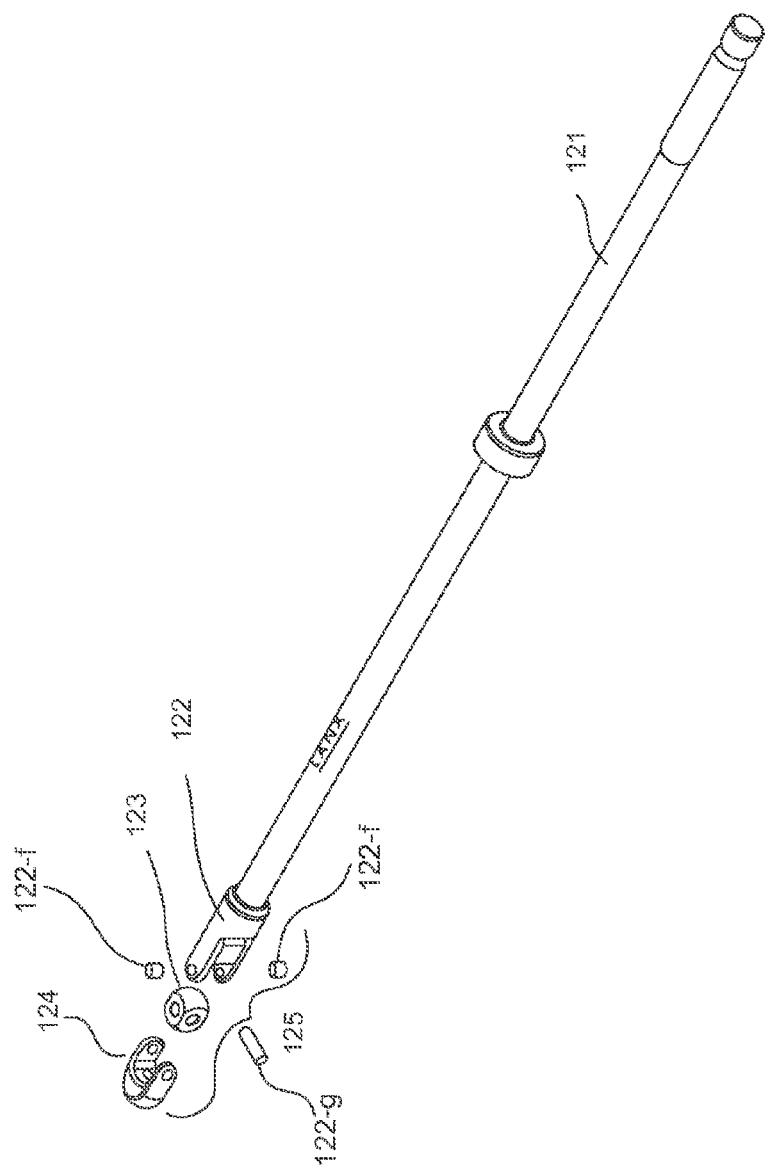
FIG. 5A is a perspective view of a shaft driver according to various embodiments described herein.
Figure 5B:
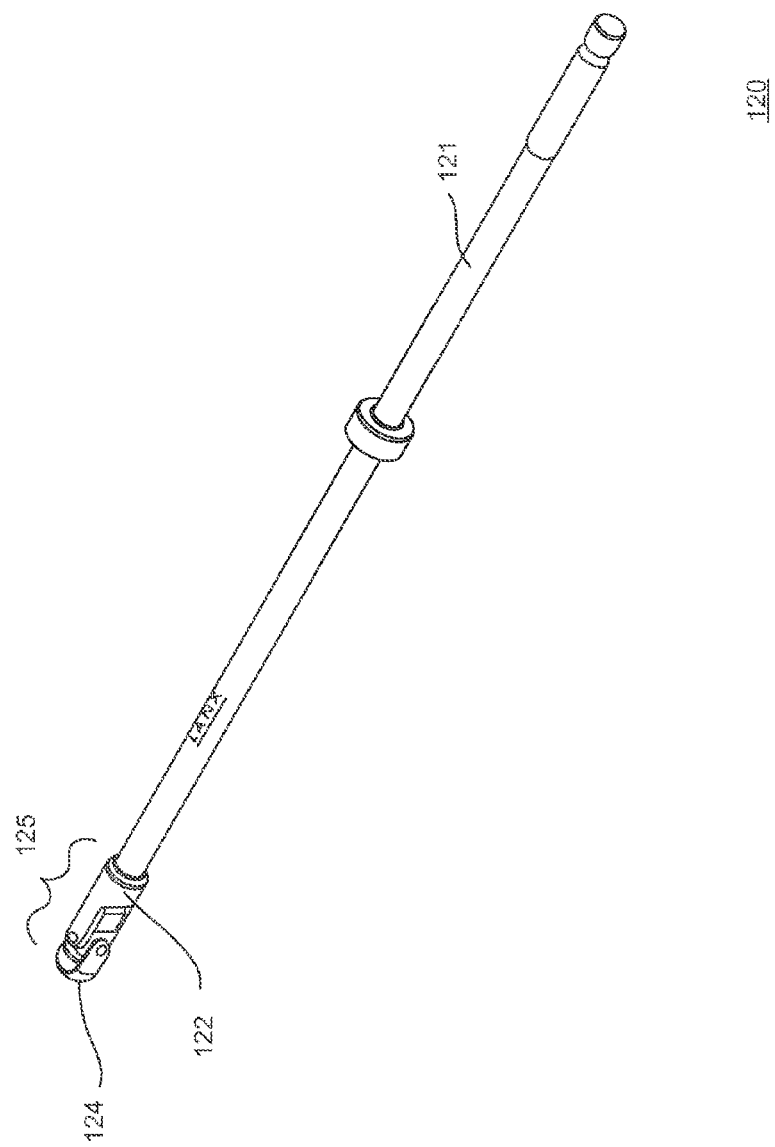
FIG. 5B is a perspective view of a shaft driver according to various embodiments described herein.

With reference to FIGS. 5A and 5B, a driver shaft 120 suitable for use with the angled sleeve 110 is shown. The driver shaft 120 includes a shaft body 121, a U-joint head 122, a block 123, and a fork 124. The U-joint head 122, block 123, and fork 124 combine to form the tool bit engagement assembly 125. The shaft body 121 is generally provided to move the tool bit engagement assembly 125 through the angled sleeve 110, including moving the tool bit engagement assembly 125 from the opening at the proximal end 110-a of the angled sleeve 110 to the angled passage segment 112 at the distal end 110-b of the angled sleeve 110. The tool bit engagement assembly 125 is configured to engage with a tool bit deposited into the angled passage segment 112 of the angled sleeve 110 via the tool bit opening 114 and provide for the rotation of the tool bit by rotating the shaft body 121.

Figure 6:
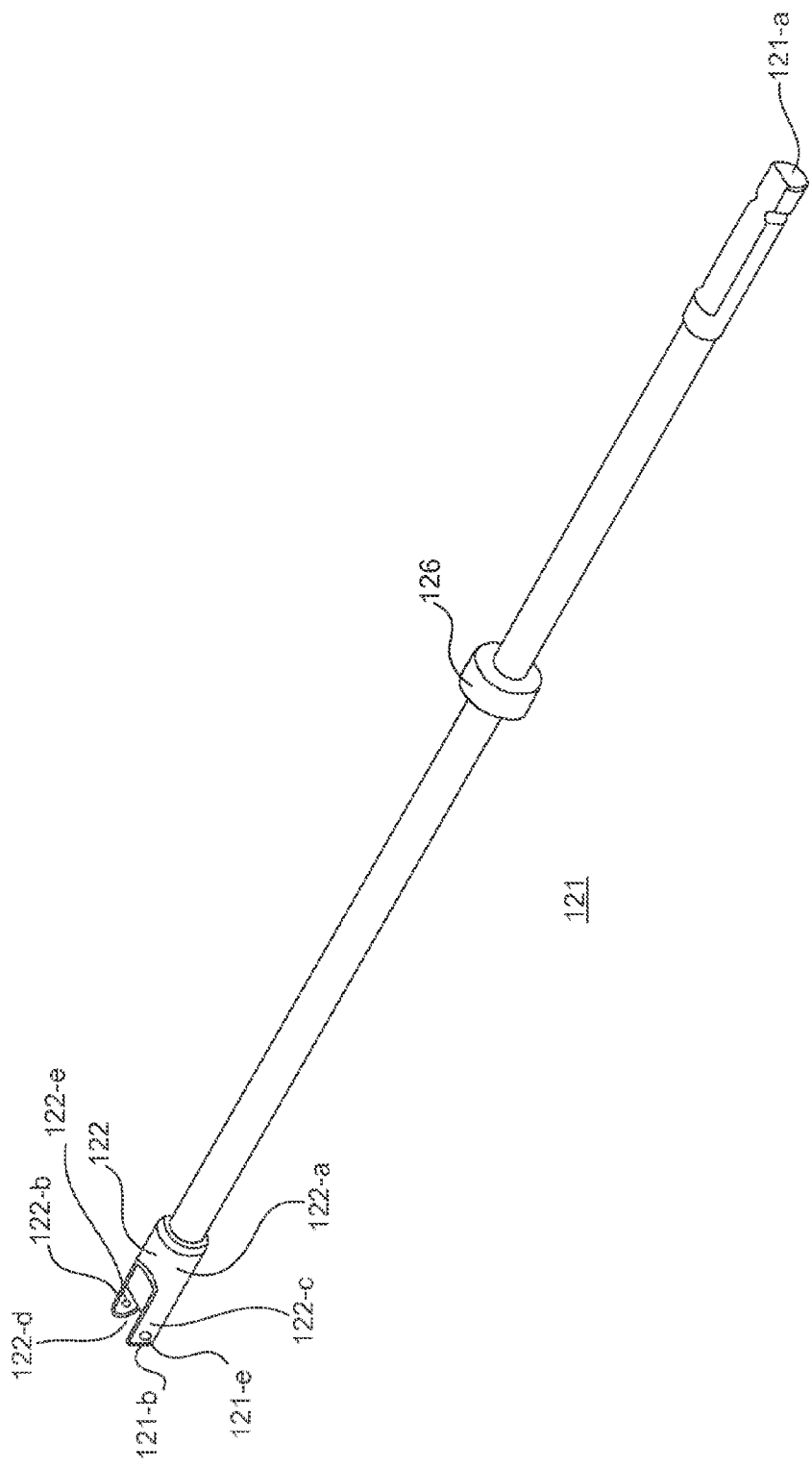
FIG. 6 is a perspective view of a shaft body and U-joint head according to various embodiments described herein.

With reference to FIG. 6, the shaft body 121 has a generally elongated cylindrical shape. At the proximal end 121-a of the shaft body 121, a portion of the cylindrical shape may be removed to form a planar surface. At the distal end 121-b of the shaft body 121, the U-joint head 122 is connected to the shaft body 121. The U-joint head 122 may be connected to the shaft body 121 using any suitable means, including forming the U-joint head 122 as part of a unitary body with the shaft body 121. The U-joint head 122 is connected with the shaft body 121 such that it does not rotate or pivot relative to the shaft body 121. At a location intermediate the proximal end 121-a and the distal end 121-b, the diameter of the shaft body 121 expands to form a disc stopper 126. The location and size of the disc stopper 126 is configured such that the disc stopper 126 will work in conjunction with the internal configuration of the angled sleeve 110 to prevent the driver shaft 120 from moving axially past a selected point within the angled sleeve 110. As best shown in FIG. 1B, the interior region of the handle 113 has an increased diameter relative to the diameter of the hollow passage way extending through the remainder of the angled sleeve 110. A ledge 113-a is thus formed where the diameter of the internal passage transitions from the large diameter to the smaller diameter. The disc stopper 126 abuts against this ledge 113-a to prevent further movement of the driver shaft 120 axially towards the distal end 110-b of the angled sleeve 110. As noted, the dimensions of the driver shaft 120, including the location of the disc stopper 126 can be selected such that when the disc stopper 126 abuts the ledge 113-a, the distal end 121-b of the driver shaft 120 (including the tool bit engagement assembly 125) is positioned at the junction 115 of the angled sleeve 110.

With continuing reference to FIG. 6, the U-joint head 122 includes a cylindrical body 122-a which tapers down at its distal end to two arms 122-b and 122-c that extend away from the cylindrical body 122-a and the shaft body 121. The two arms 122-b and 122-c extend from the periphery of the cylindrical body 122-a and are oriented generally parallel to one another and to the axis of the shaft body 121. The two arms 122-b and 122-c are relatively thin such that a gap 122-d is defined between the two arms 122-b and 122-c that is only slightly smaller than the diameter of the cylindrical body 122-a. A bore 122-e is provided at the rounded terminal end of each arm 122-b and 122-c. The bores 122-e are aligned with one another such that one pin 122-f (shown in FIG. 5A) can be inserted through each bores and extend into the gap 122-d at an orientation perpendicular to the axis of the shaft body 121. As discussed in greater detail below, the gap 122-d in the U-joint head 122 is sized and configured so that a block 123 can be positioned within the gap 122-d and between the two arms 122-b and 122-c. The block 123 is pivotal about an axis defined by the pins 122-f.

Figure 7:
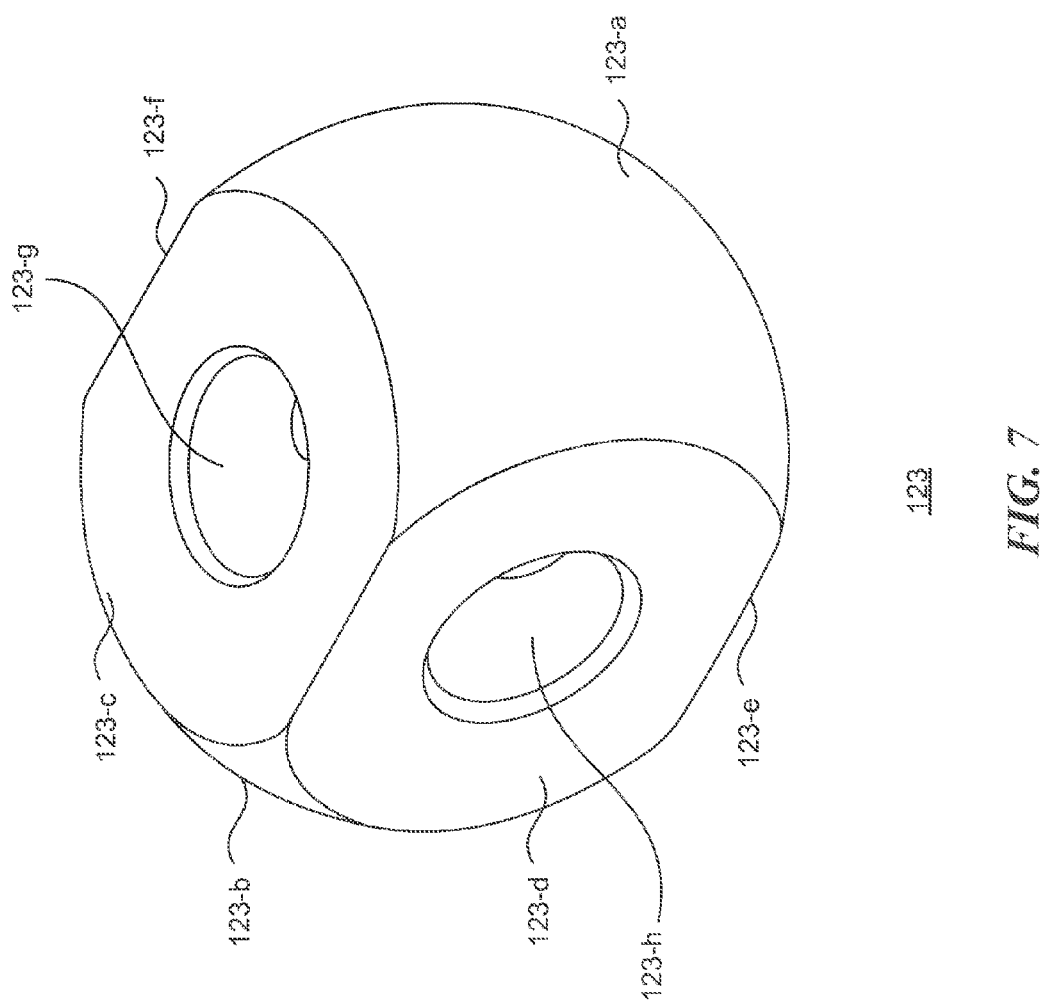
FIG. 7 is a perspective view of a block suitable for use with a driver shaft according to various embodiments described herein.

With reference to FIG. 7, the block 123 has a generally cube shape. Two opposing sides 123-a and 123-b of the block 123 are substantially rounded, which results in the edges of the block that contact the rounded sides 123-*a* and 123-*b* also be rounded. The remaining sides 123-*c*, 123-*d*, 123-*e*, and 123-*f* of the block are planar. As shown in FIG. 7, planar side 123-*c* is opposite planar side 123-*e* and planar side 123-*d* is opposite planar side 123-*f*. A through hole 123-*g* extends from planar side 123-*c* to planar side 123-*e* and a through hole 123-*h* extends from planar side 123-*d* to planar side 123-*f*. The through holes 123-*g* and 123-*h* are configured to receive pins or rods that will allow the fork 124 to pivot along two perpendicular axes when the tool bit engagement assembly 125 is assembled.

Figure 8:
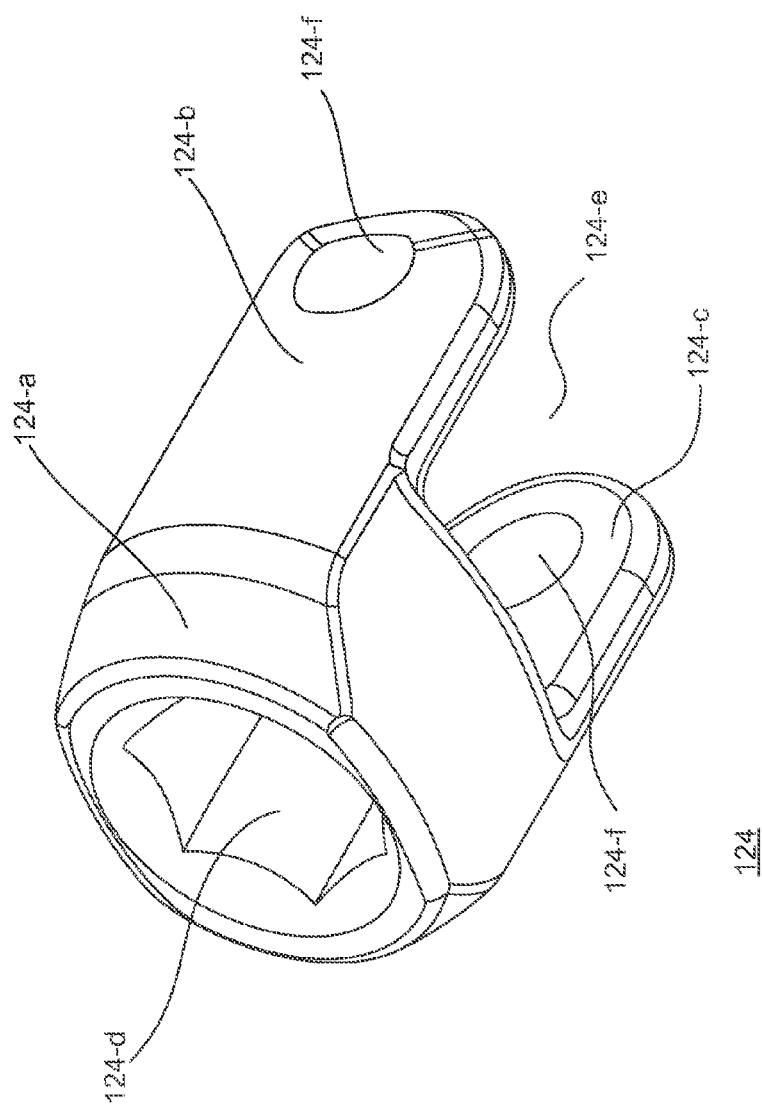
FIG. 8 is a perspective view of a fork suitable for use with a driver shaft according to various embodiments described herein.

With reference to FIG. 8, the fork 124 includes a body portion 124-*a* having a generally cylindrical shape and two arms 124-*b* and 124-*c* that extend away from the body portion 124-*a*. The two arms 124-*b* and 124-*c* extend from the periphery of the body portion 124-*a* and are oriented generally parallel to one another and to the axis of the body portion 124-*a*. The two arms 124-*b* and 124-*c* are relatively thin such that a gap 124-*e* is defined between the two arms 124-*b* and 124-*c* that is only slightly smaller than the diameter of the body portion 124-*a*. A bore 124-*f* is provided at the rounded terminal end of each arm 124-*b* and 124-*c*. The bores 124-*f* are aligned with one another such that a rod 122-*g* (shown in FIG. 5A) can be inserted through both bores 124-*f* and extend across the gap 124-*e* at an orientation perpendicular to the axis of the body portion 124-*a*. The gap 124-*e* in the fork 124 is sized and configured so that the block 123 can be positioned within the gap and between the two arms 124-*b* and 124-*c*. The fork 124 is pivotal about an axis defined by the rod 122-*g*.

It is noted that, in some embodiments, the set of pins can be used to form a pivotal connection between the fork 124 and the block 123 and the rod can be used to form a pivotal connection between the block 123 and the U-joint head 122.

Figure 15:
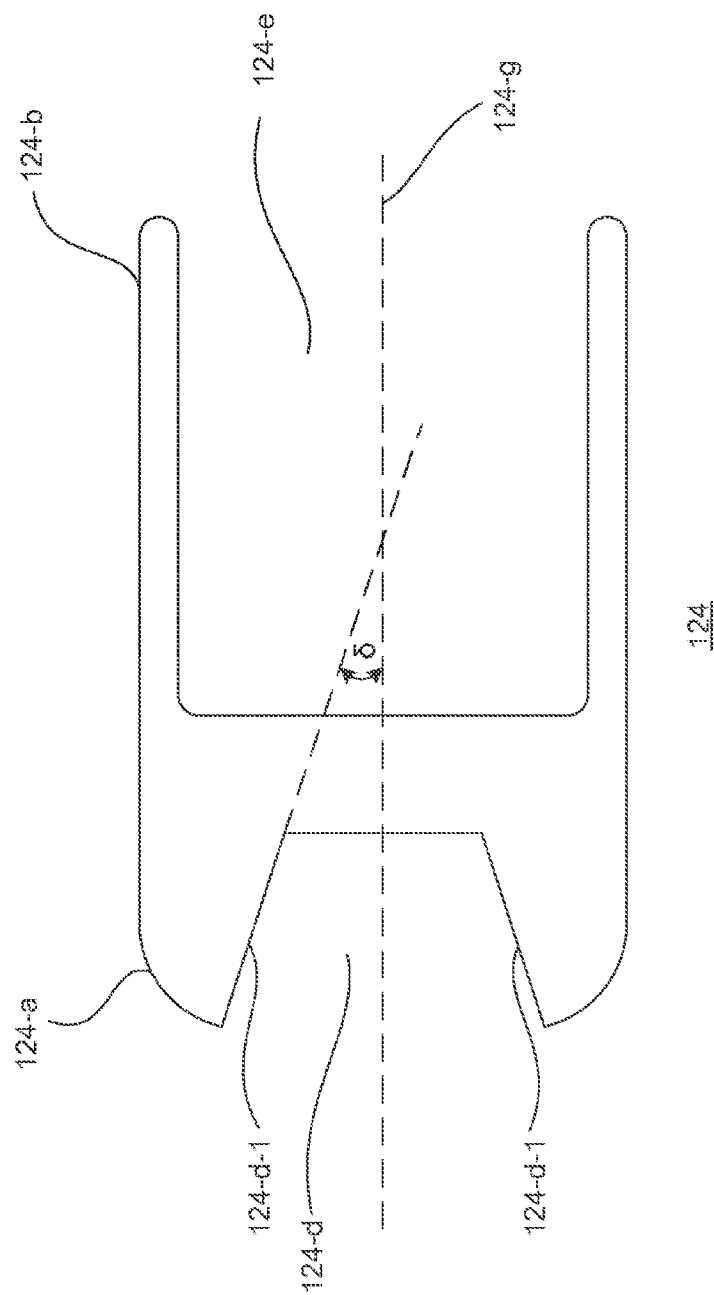
FIG. 15 is a cross sectional view of the fork shown in FIG. 8.

The fork 124 further includes a recess 124-*d* (or female socket) in the body portion 124-*a*. The opening of the recess 124-*d* is at the end of the body portion 124-*a* opposite where the arms 124-*b* and 124-*c* extend away from the body portion 124. The recess 124-*d* is configured for receiving the male end of a tool bit that is engaged by the fork 124. The recess can have any shape suitable for engaging a tool bit. As shown in FIG. 8, the recess has a hexagonal shape for receiving a hexagonal-shaped male end of a tool bit. As shown in FIG. 15, the recess 124-*d* has angled sidewalls 124-*d*-1. In some embodiments, the sidewalls 124-*d*-1 are form an angle DELTA with the longitudinal axis 124-*g* of the fork 124. In some embodiments, the angle DELTA is in the range of from 0.1° to 5°. The angled side walls 124-*d*-1 of the recess 124-*d* can improve the ease with which a tool bit engagement body can be disengaged from the recess 124-*d*.

Referring back to FIGS. 5A and 5B, the assembled tool bit engagement assembly 125 is shown. The block 123 is inserted into the gap 122-*d* of the U-joint head 122 such that two opposing planar sides of the block 123 are flush with the arms 122-*b* and 122-*c* of the U-joint head 124. Additionally, the through hole of the block 123 is aligned with the bores 122-*e* in the arms 122-*b* and 122-*c* so that a short pin can be inserted through each hole 122-*e* and partially into the opening of the through hole 123-*h* adjacent each respective bore 122-*e*. This pivotably secures the block 123 to the U-joint head 122. Similarly, the fork 124 is positioned so that the block 123 is inserted into the gap 124-*e* in the fork 124. As shown in FIGS. 5A and 5B, the fork 124 is oriented such that the arms 124-*b* and 124-*c* are flush mounted with the remaining planar sides of the block 123 (i.e., the planar sides of the block 124 not flush mounted with the arms 122-*b* and 122-*c* of the U-joint head 122. The bores 124-*f* in the arms 124-*b* and 124-*c* are aligned with the through hole 123-*g* in the block 123 and a single rod extends through both bores 124-*f* and the through hole 123-*g* to pivotably secure the fork 124 to the block 123.

It is noted that two long rods could be used to pivotally secure the U-joint head 122 to the block 123 and the block 123 to the fork 124, but that such a configuration would require two through holes through the block 123 that do not intersect. Other manners of pivotally securing the U-joint head 122 to the block 123 and the block 123 to the fork 124 include a single long rod and two short pins (as described above) or four short pins (two for the U-joint head and two for the fork).

Thus assembled, the fork 124 is able to pivot in two directions, namely about the axis of each of the two through holes in the block 123. As a result of this configuration, the fork 124 can be rotated by rotating the shaft body 121 even when the fork 124 is positioned at an angle within the angled passage segment 112 of the angled sleeve 110. Accordingly, when the fork 124 is engaged with a tool bit, the rotation of the shaft body 121 results in the rotation of the tool bit and the ability to drive a screw with the tool bit.

Figure 9:
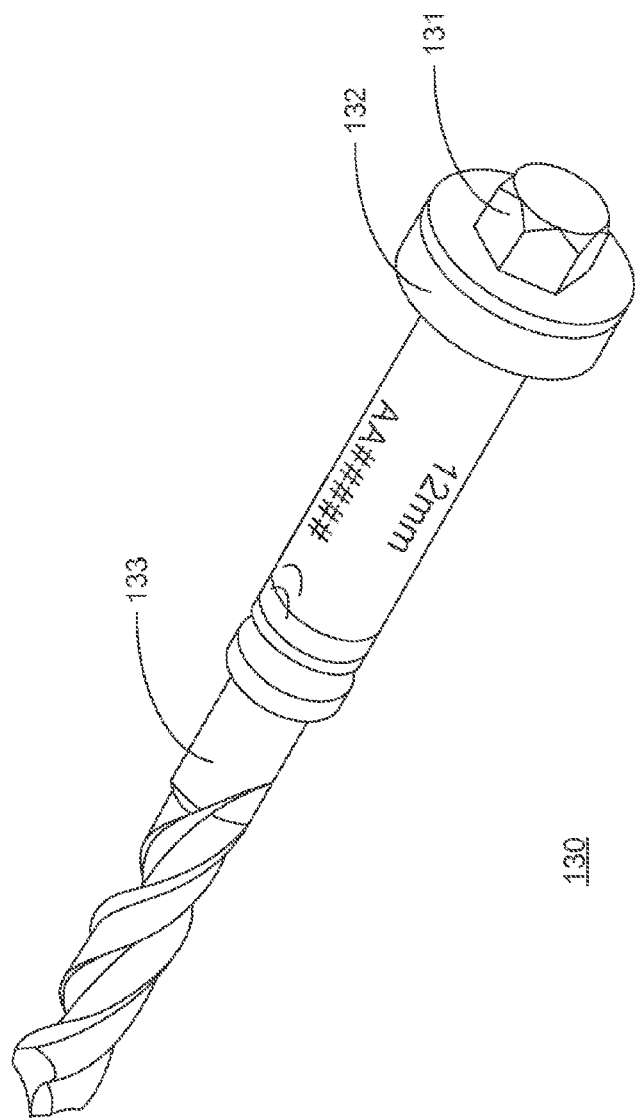
FIG. 9 is a perspective view of a tool bit according to various embodiments described herein.

With reference to FIG. 9, a tool bit 130 is provided to be used in conjunction with the angled sleeve 110 and the driver shaft 120. As discussed above, the tool bit 130 is passed through the tool bit opening 114 in the angled sleeve 110 so that the tool bit 130 can pass directly into and through the angled passage segment 112 of the angled sleeve 110. The tool bit 130 is dimensioned so that it will fit through both tool bit opening 114 and the angled passage segment 112.

The tool bit 130 generally includes an engagement body 131, a stopper 132, and a tool body 133, which is shown as a drill bit in the exemplary embodiment. The engagement body 131 (or male connector) is located at the proximal end of the tool bit 130 and is shaped and dimensioned to cooperatively engage with the recess 124-*d* (or female socket) of the fork 124. As shown in FIG. 9, the engagement body 131 has a hexagonal shape that is suitable for engaging with the hexagonal recess 124-*d* shown in FIG. 8. In some embodiments, the engagement body 131 will also have a length approximately equal to the depth of the recess 124-*d*. The engagement body is not limited to a hexagonal shape. Any shape can be used provided that the shape of the engagement body 131 suitably mates with the recess 124-*d* so that rotation of the fork 124 results in corresponding rotation of the tool bit 130.

Figure 10:
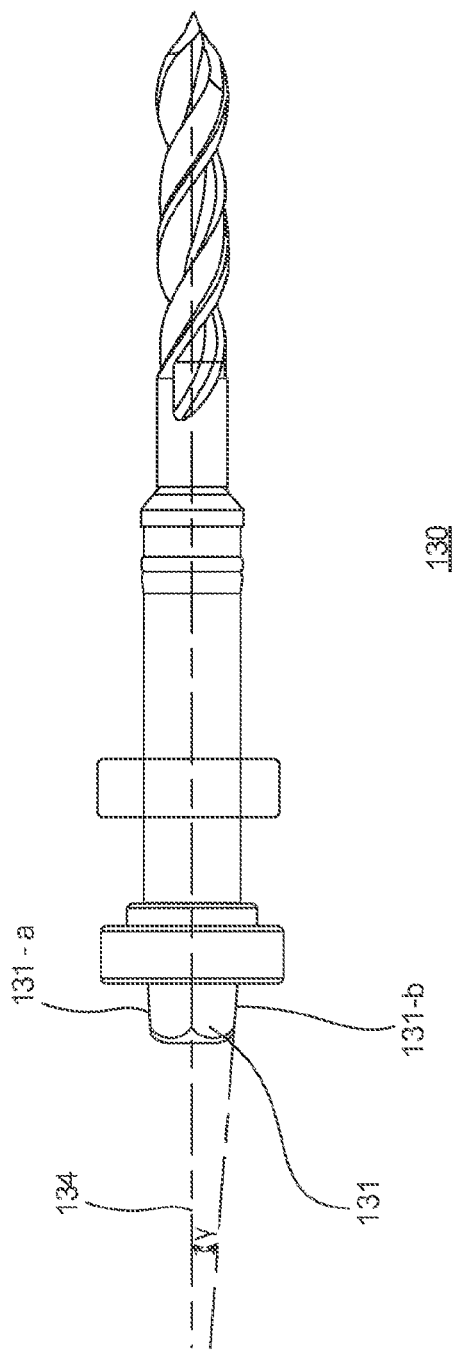
FIG. 10 is a cross sectional view of the tool bit illustrated in FIG. 9.

With reference to FIG. 10, the engagement body 131 has a plurality of side walls 131-*a* to 131-*f* for the hexagonal engagement body shown. Each of the side walls, including side wall 131-*a* and 131-*b*, of the engagement body 131 are angled slightly to assist with the insertion and removal of the male body into the female socket. As shown in FIG. 10, the tool bit 130 has an axis 134. The side walls of the engagement body 131 form an angle GAMMA with the axis 134. The angle GAMMA can be in the range of from 0.1° to 5°. By angling each of the side walls of the engagement body 131 in this manner, it becomes easier to separate the fork 124 from the engagement body 131 when the driver shaft 120 is pulled out of the angled sleeve 110.

Referring back to FIG. 9, the tool bit 130 includes a stopper 132. The stopper 132 is located intermediate the proximal and distal ends of the tool bit 130 and has a generally disc shape. The stopper 132 has a diameter that is larger than the remainder of the tool bit 130. The stopper is generally used to prevent that tool bit 130 from sliding completely out of the distal end of the angled passage segment 112 of the angled sleeve 110. For example, as shown in FIG. 1B, the distal end of the angled passage segment 112 has an opening 112-*a* that is large enough for the tool body 133 to pass through, but which is smaller than the stopper 132. In this manner, the stopper 132 abuts against the walls of the opening 112-*a* and prevents the tool bit 132 from passing all the way out of the angled passage segment 112. The location of the stopper 132 along the length of the tool bit 130 can be selected based on the dimensions of the angled passage segment 112 so that the stopper 132 allows a sufficient amount of the tool body 133 to pass through the angled passage segment 112 and positions the engagement body 131 within the angled passage segment 112 such that the fork 124 can engage with the engagement body 131.

Figure 11:
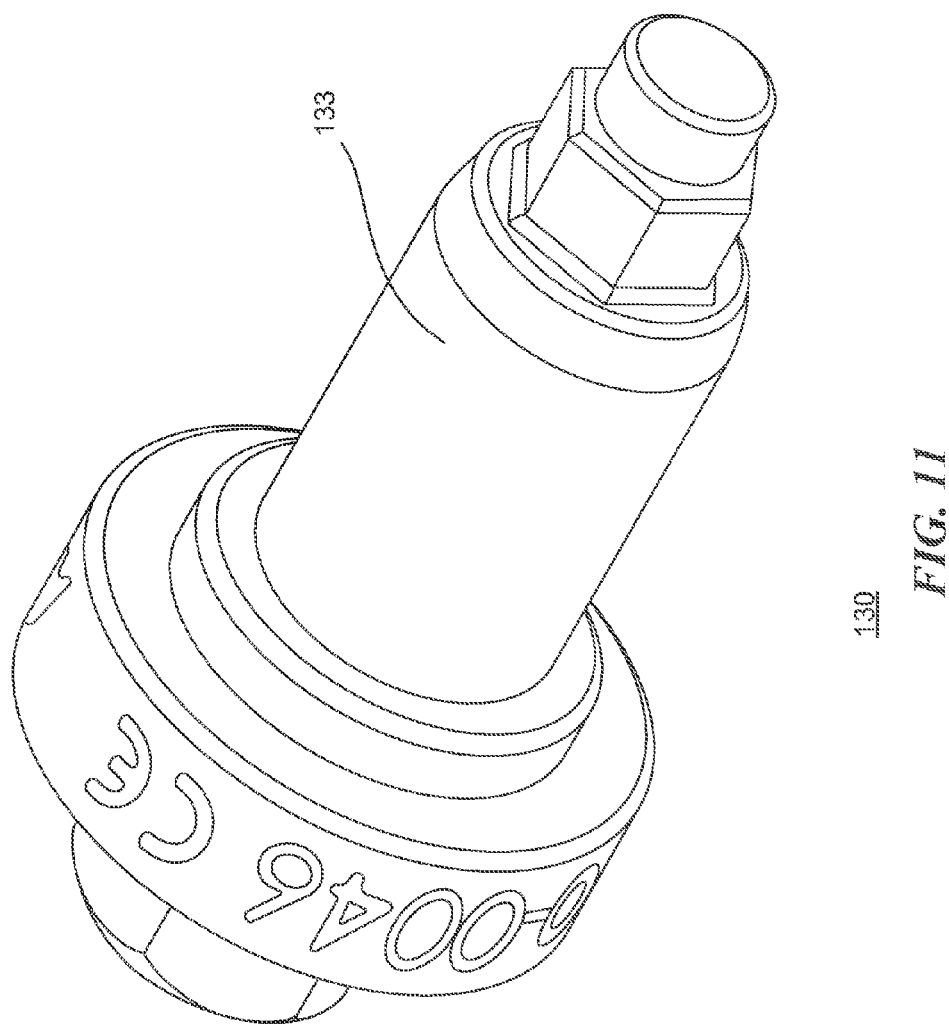
FIG. 11 is a perspective view of a tool bit according to various embodiments described herein.

The tool body 133 is generally located at the distal end of the tool bit 130. The exact shape of the tool body 133 is generally not limited and can include any of a variety of different tool shapes, including, but not limited to, screws, drills and taps. FIG. 9 shows a tool body 133 that is a drill. FIG. 11 illustrates a tool bit 130 having a tool body 133 that is a solid tip driver.

Figure 12:
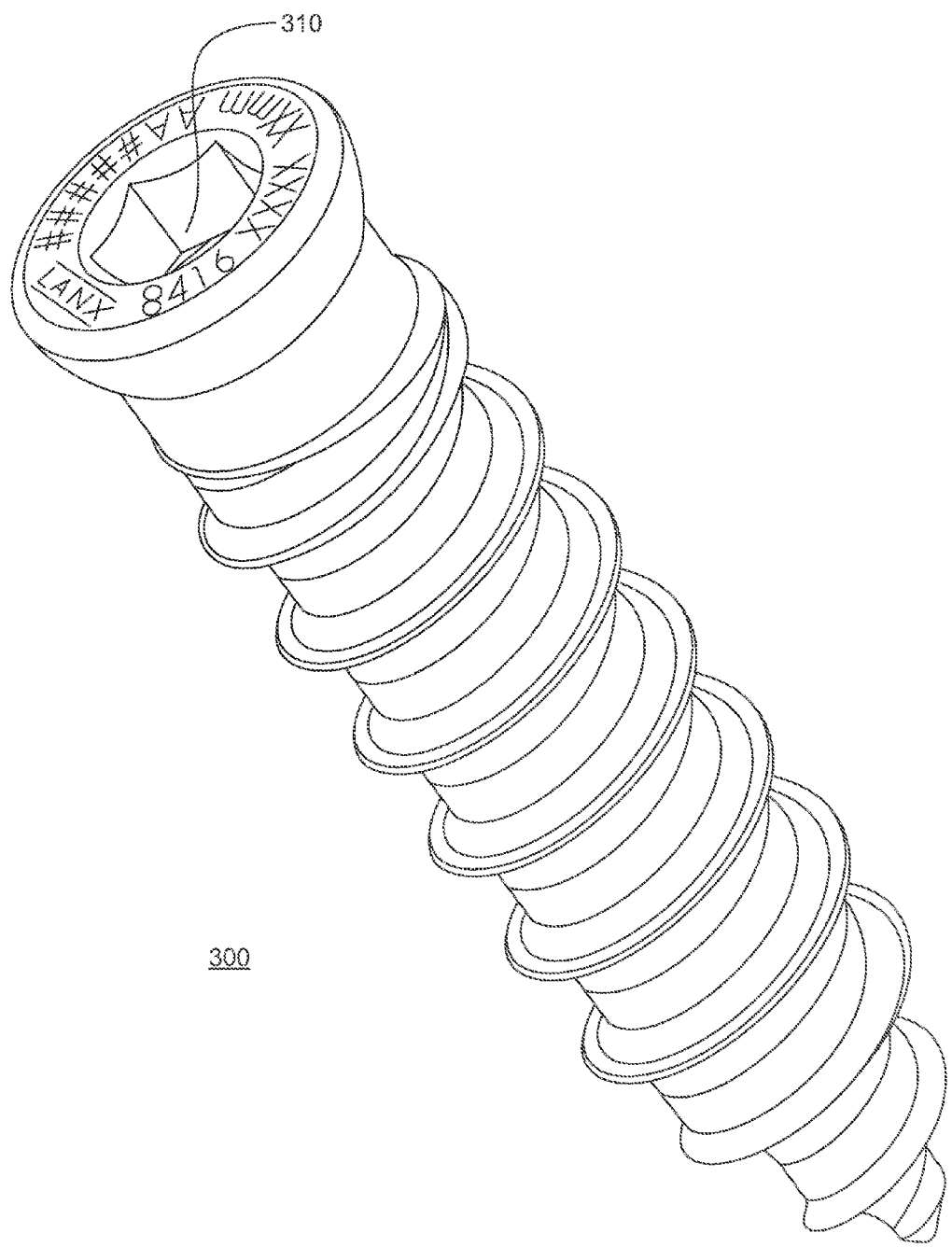
FIG. 12 is a perspective view of a tool bit according to various embodiments described herein.

In a variation on the above described embodiments, the fork 124 replaces the recess with an engagement body and the tool bit replaces the engagement body with a recess. In such configurations, the fork 124 includes the male engagement body and the tool bit includes the female engagement body. In FIG. 12, a tool bit 300 is shown having a recess 310 instead of an engagement body.

In application, the angled instrument assembly can be used by first providing a passage to the target site or an area near the target site in the bone. The passage can be created using any methods known to those of ordinary skill in the art. The angled sleeve can then be prepared for insertion into passage. In some embodiments, the angled sleeve is prepared by inserting the selected tool bit into angled passage segment via the tool bit opening and then inserting the driver shaft into the angled sleeve. The tool bit can be inserted into the angled passage section such that the stopper on the tool bit rests against the opening in the distal end of the angled passage segment and the majority of the tool body of the tool bit extends out of the opening in the distal end of the angled passage segment. The driver shaft can be inserted into the angled sleeve such that the tool bit engagement assembly is engaged with the tool bit positioned at the distal end of the angled sleeve. In some embodiments, the stopper on the driver shaft will engage with the ledge at the distal end of the handle region to ensure that the driver shaft is not inserted too far into the angled sleeve. As the fork at the distal end of the driver shaft engages the junction of the angled sleeve, the junction deflects the fork and causes it to pivot so that it can become aligned in parallel with the axis of the angled passage segment. This can help to ensure that the recess in the fork is properly aligned to receive the engagement body of the tool bit. Additionally, the configuration of the tool bit opening, including its size and locations, ensures that the fork does not get caught on the distal end of the opening as it is being moved through the junction.

Once the tool bit and the driver shaft are so positioned, the angled sleeve can be moved through the passage and towards the target site. The angled sleeve and be maneuvered in any suitable manner that allows the distal end of the angled sleeve to provide access to the target site. In some embodiments, this may involve inserting the angled sleeve into the passage and pivoting, rotating, and angling the angled sleeve until the distal end of the angled sleeve is positioned at the target site.

Once positioned within the passage, the driver shaft can be rotated in order to rotate the fork and the engaged tool bit. In some embodiments, the driver shaft is rotated by using the handle provided at the proximal end of the angled sleeve. This handle may include an internal mechanism that engages with the driver shaft inserted into the angled sleeve so that rotating the handle on the angled sleeve also rotates the driver shaft. The rotating action can be carried out manually or with the assistance of a powered drill. The rotating motion can be carried out for as long as necessary to carry out the desired action (e.g., drilling a hole or driving a screw).

Although examples of an angled instrument assembly and associated techniques have been described and illustrated in detail, it is to be understood that the same is intended by way of illustration and example only and is not to be taken by way of limitation. Accordingly, variations in and modifications to the angled instrument assembly and techniques will be apparent to those of ordinary skill in the art.

We claim:

1. An angled instrument assembly comprising:
   an angled sleeve having a hollow passage extending therethrough, comprising:
      a straight passage segment having a first longitudinal axis and an interior surface;
      an angled passage segment having a second longitudinal axis and an interior surface; and
      a junction region connecting the straight passage segment to the angled passage segment, the junction region including an inner elbow and an outer elbow;
      wherein the second axis forms a first angle with the first axis; and
      wherein an interior surface of the inner elbow comprises a surface that forms a second angle with the first axis, the second angle being less than the first angle; and
   a driver shaft configured to be received within the hollow passage of the angled sleeve, comprising:
      an elongated shaft body having a proximal end and a distal end; and
      a tool bit engagement assembly coupled at the distal end of the elongated shaft body,
      wherein the angled sleeve further comprises a tool bit opening located at the outer elbow of the junction region and configured to allow a tool bit to be passed into the angled passage segment along the second axis.

2. The angled instrument assembly as claimed in claim 1, further comprising:
   a tool bit comprising a proximal end and a distal end, the proximal end including an engagement body configured for engaging with the tool bit engagement assembly.

3. The angled instrument assembly as claimed in claim 2, wherein the engagement body comprises three or more planar side walls and an end wall and the surface of each of the planar side walls forms an angle with an axis of the tool bit, the angle being in the range of from 1° to 5°.

4. The angled instrument assembly as claimed in claim 2, wherein the tool bit engagement assembly comprises:
   a fork having a proximal end and a distal end and wherein the distal end of the fork includes a recess configured for receiving the engagement body of the tool bit.

5. The angled instrument assembly as claimed in claim 4, wherein the tool bit engagement assembly is configured to permit the fork to pivot along two perpendicularly oriented axes.

6. The angled instrument assembly as claimed in claim 2, wherein the tool bit engagement assembly comprises:
   a U-joint head having a body and two arms extending away from the body in a distal direction and defining a gap between the two arms;
   a fork having a body, two arms extending away from the body in a proximal direction and defining a gap between the two arms, and a recess formed in a distal end of the fork; and
   a pivot block simultaneously positioned within the gap of the U-joint head and the fork, the pivot block having a first through hole extending between a first pair of opposing sides of the block and a second through hole extending between a second pair of opposing sides of the block;

wherein a connection rod extends through the first through hole and mates with the two arms of the U-joint head to pivotally connect the pivot block to the U-joint head; and wherein a connection pin is inserted into each opening of the second through hole and mates with one of the two arms of the fork to pivotally connect the pivot block to the fork.

7. The angled instrument assembly as aimed in claim 1, wherein the angled sleeve further comprises a handle mechanism located at a proximal end of the angled sleeve and configured to rotate the driver shaft when the driver shaft is received within the hollow passage of the angled sleeve.

8. An angled sleeve having a hollow passage extending therethrough comprising:

an elbow section having an inner elbow interior surface, wherein the inner elbow interior surface comprises a first surface segment, a second surface segment, and a third surface segment, with the second surface segment being located between the first surface segment and the third surface segment;

wherein the first surface segment is oriented at 0°, the third surface segment is oriented at an angle in the range of from 1° to 45°, and the second surface segment is oriented at an angle greater than the first surface segment but less than the third surface segment, and wherein the elbow section further includes an outer elbow wall and wherein a tool bit opening is formed in the outer elbow wall.

9. The angled sleeve as claimed in claim 8, further comprising:

an angled passage section extending from a distal end of the elbow section and having a uniform diameter throughout the length of the angled passage section.

10. The angled sleeve as claimed in claim 9, wherein the angled passage section includes a distal opening having a diameter that is less than the diameter of the angled passage section.

11. The angled sleeve as claimed in claim 8, wherein the angled passage section has an axis that is oriented parallel to the third surface segment of the inner elbow interior surface.

12. The angled sleeve as claimed in claim 8, further comprising a straight passage section extending from the proximal end of the elbow section.

13. The angled sleeve as claimed in claim 12, wherein the straight passage section includes a handle positioned at a proximal end of the straight passage section.

14. The angled sleeve as claimed in claim 13, wherein the handle is configured to engage a driver shaft received within the straight passage section and rotate the driver shaft when the handle is rotated.

15. The angled sleeve as claimed in claim 8, wherein the straight passage section has an axis that is oriented parallel to the first surface segment of the inner elbow interior surface.

16. An angled sleeve having a hollow passage extending therethrough comprising:

an elbow section having an inner elbow interior surface, wherein the inner elbow interior surface comprises a first surface segment, a second surface segment, and a third surface segment, with the second surface segment being located between the first surface segment and the third surface segment; and an angled passage section extending from a distal end of the elbow section and having a uniform diameter throughout the length of the angled passage section, the angled passage section including a distal opening having a diameter that is less than the diameter of the angled passage section, wherein the elbow section includes a first axis corresponding to the first surface segment and oriented at 0° and a third axis corresponding to the third surface segment and orientated at an angle in a range from 1° to 45° and a second axis corresponding to the second surface segment and oriented at an angle greater than the first axis but less than the third axis.

* * * * *